United States Patent [19]
Van Kruchten

[11] Patent Number: 6,124,508
[45] Date of Patent: Sep. 26, 2000

[54] QUATERNARY PHOSPHONIUM SALT CATALYSTS IN CATALYTIC HYDROLYSIS OF ALKYLENE OXIDES

[75] Inventor: Eugene Marie Godfried Andre Van Kruchten, Amsterdam, Netherlands

[73] Assignee: Shell Oil Company, Houston, Tex.

[21] Appl. No.: 09/457,534

[22] Filed: Dec. 9, 1999

[30] Foreign Application Priority Data

Dec. 14, 1998 [EP] European Pat. Off. .............. 98204232

[51] Int. Cl.[7] .............................. C07C 29/10; C07F 9/02; B01J 35/08
[52] U.S. Cl. .................................. 568/867; 568/9; 502/11
[58] Field of Search ............................. 568/867, 9; 502/11

[56] References Cited

U.S. PATENT DOCUMENTS

| | | | |
|---|---|---|---|
| 4,160,116 | 7/1979 | Mieno et al. ........................... | 568/867 |
| 4,982,021 | 1/1991 | Best et al. ............................... | 568/867 |

FOREIGN PATENT DOCUMENTS

| | | | |
|---|---|---|---|
| 0156449 A2 | 10/1985 | European Pat. Off. ........ | C07C 29/10 |
| 0160330 A1 | 11/1985 | European Pat. Off. ........ | C07C 31/20 |
| 0226799 B1 | 7/1987 | European Pat. Off. ........ | C07C 29/10 |
| 2086894 | 5/1982 | United Kingdom . | |
| WO 95/20559 | 8/1995 | WIPO ............................ | C07C 29/10 |

OTHER PUBLICATIONS

International Search Report of Mar. 3, 2000.

*Primary Examiner*—Samuel Barts
*Assistant Examiner*—Brian J. Davis

[57] ABSTRACT

A process for the preparation of alkylene glycols by reacting an alkylene oxide with water in the presence of at least one ionic composition of a quaternary phosphonium cation of the general formula $$R_1R_2R_3R_4P^+$$

Whereby each of $R_1$, $R_2$, $R_3$ and $R_4$, independently, may be an alkyl, cycloalkyl, aryl, alkylaryl or arylalkyl group having from 1 to 10 carbon atoms, each of which may carry one or more substituents, or be attached to a polymer and an anion other than metalate or halogen.

5 Claims, No Drawings

QUATERNARY PHOSPHONIUM SALT CATALYSTS IN CATALYTIC HYDROLYSIS OF ALKYLENE OXIDES

1. FIELD OF THE INVENTION

The present invention relates to a process for the preparation of alkylene glycols by reacting an alkylene oxide with water in the presence of a catalytic composition.

2. BACKGROUND OF THE INVENTION

Alkylene glycols, in particular monoalkylene glycols, are of established commercial interest. For example, monoalkylene glycols are being used in anti-freeze compositions, as solvents and as base materials in the production of polyalkylene terephthalates e.g. for fibres or bottles.

The production of alkylene glycols by liquid phase hydrolysis of alkylene oxide is known. The hydrolysis is performed without a catalyst by adding a large excess of water, e.g. 20 to 25 moles of water per mole of alkylene oxide, or it is performed with a smaller excess of water in a catalytic system. The reaction is considered to be a nucleophilic substitution reaction, whereby opening of the alkylene oxide ring occurs, water acting as the nucleophile. Because the primarily formed monoalkylene glycol also acts as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Considerable efforts have been made to find an alternative for increasing the reaction selectivity without having to use a large excess of water. Usually these efforts have focused on the selection of more active hydrolysis catalysts and various catalysts have been disclosed.

Both acid and alkaline hydrolysis catalysts have been investigated, whereby it would appear that the use of acid catalysts enhances the reaction rate without significantly affecting the selectivity, whereas by using alkaline catalysts generally lower selectivities with respect to the monoalkylene glycol are obtained.

Certain anions, e.g. bicarbonate (hydrogen carbonate), bisulphite (hydrogen sulphite), formate and molybdate, are known to exhibit good catalytic activity in terms of alkylene oxide conversion and selectivity towards monoalkylene glycol. However when the salts of these anions are used as the catalyst in a homogeneous system, work-up of the reaction product by distillation will pose a problem because the salts are poorly soluble in the glycol and tend to make it semi-solid. Quaternary ammonium salts remain soluble in the glycol reaction product.

High conversions, good selectivity and a low water/alkylene oxide ratio can be obtained with the process, disclosed in EP-A 0 156 449 and EP-A 0 160 330 (both of Union Carbide). According to these documents the hydrolysis of alkylene oxides is carried out in the presence of a selectivity-enhancing metalate anion-containing material, preferably a solid having electropositive complexing sites having affinity for the metalate anions. The said solid is preferably an anion exchange resin, in particular a styrene-divinyl benzene copolymer. The electropositive complexing sites are in particular quaternary ammonium, protonated tertiary amine or quaternary phosphonium. No specific advantage is attributed to the quaternary phosphonium. The metalate anions are specified as molybdate, tungstate, metavanadate, hydrogenpyrovanadate and pyrovanadate anions. A complication of this process is that the alkylene glycol-containing product stream also comprises a substantial amount of metalate anions, displaced from the electropositive complexing sites of the solid metalate anion containing material. In order to reduce the amount of metalate anions in the alkylene glycol product stream, this stream is contacted with a solid having electropositive complexing sites associated with anions which are replaceable by the said metalate anions.

In WO 95/20559 (Shell) there is disclosed a process for the preparation of alkylene glycols wherein an alkylene oxide is reacted with water in the presence of a catalyst composition comprising a solid material having one or more electropositive sites, which are coordinated with one or more anions other than metalate or halogen anions, e.g. bicarbonate, bisulphite and carboxylate, with the proviso that when the solid material is an anionic exchange resin of the quaternary ammonium type and the anion is bicarbonate the process is performed in the substantial absence of carbon dioxide. According to this document, the presence of carbon dioxide in the feed is detrimental to the catalytic effect of bicarbonate-exchanged resins of the quaternary ammonium type.

As indicated above, salts composed of catalytic anions and quaternary ammonium cations can be used in a homogeneous system as well as in a heterogeneous system. Indeed, in heterogeneous systems such quaternary ammonium ions are the traditionally used cations of most anion exchange resins. A drawback shared by these quaternary ammonium compounds is their limited tolerance to heat. In practising the process of alkylene oxide hydrolysis according to WO 95/20559 with catalyst compositions based on conventional organic quaternary ammonium ion exchangers it has been found, that under severe alkylene oxide hydrolysis reaction conditions (high temperature and/or long service) the catalytic activity (selectivity and/or conversion) and/or swelling behaviour of the conventional resin-based catalysts tends to deteriorate.

In U.S. Pat. No. 4,160,116 (Showa Denko) there is disclosed a process for the production of an alkylene glycol by hydrating an alkylene oxide in the presence a substantial amount of carbon dioxide using a quaternary phosphonium salt of iodine, bromide or chlorine as a catalyst.

3. SUMMARY OF THE INVENTION

The present invention relates to a process for the preparation of alkylene glycols by reacting an alkylene oxide with water in the presence of at least one ionic composition of a quaternary phosphonium cation of the general formula $$R_1R_2R_3R_4 P^+$$

Whereby each of $R_1$, $R_2$, $R_3$ and $R_4$, independently, may be an alkyl, cycloalkyl, aryl, alkylaryl or arylalkyl group having from 1 to 10 carbon atoms, each of which may carry one or more substituents or be attached to a polymer, and an anion other than metalate or halogen.

The anion is preferably chosen from the group of bicarbonate, bisulphite and the carboxylic acid derivatives. When the anion is a carboxylic acid, it is preferably chosen from the group of formate and citrate.

Generally, carbon dioxide is not required.

In a preferred embodiment of the present invention, the quaternary phosphonium cation is immobilised on a solid support, such as an anion exchange resin.

4. DETAILED DESCRIPTION OF THE INVENTION

As such, the quaternary phosphonium compounds as herein defined are effective as alkylene oxide hydrolysis catalysts in a homogeneous liquid reaction system. However, a particular advantage of these quaternary phosphonium compounds emerges when they are used in a heterogeneous reaction system, wherein the quaternary phosphonium cations constitute the electropositive sites of a solid support, as defined in WO 95/20559. In particular, when the solid support is a strongly basic anionic exchange resin the base of which is a quaternary phosphonium cation according to the present invention, a catalytic composition is formed—with the anion according to the invention—which is stable and which retains its selectivity and stability under severe reaction conditions as well as being more resistant to swelling.

Any of a large number of ion exchange resin (IER) types can be used as the solid support, in particular the strongly basic (anionic) IER's wherein the basic groups are quaternary phosphonium groups attached (i.e. adsorbed, reacted or grafted) to a polymeric backbone. Suitable polymeric backbones include high molecular weight polymers and co-polymers, e.g. addition and condensation polymers, including polyalkylene, polyester, polycarbonate, polyurethane, formaldehyde resins, etc. Commercially available IER's include resins based on polyacrylate or styrene-divinylbenzene copolymers. Many of these IER's are purely organic polymers, but also silica based resins, such as polysiloxanes, can conveniently be used. Alternative materials having the quaternary phosphonium type of electropositive complexing site bonded by adsorption, reaction or grafting, include those of inorganic nature, such as carbon, silica, silica-alumina, zeolites, glass and clays such as hydrotalcite.

The catalyst composition according to the invention can be completed by immobilisation of the catalytically active anion on the solid support by adding it in aqueous solution to a suspension of the solid support, which may or may not be adapted in a foregoing preparatory step. For example, when the solid support is an anionic exchange resin the immobilisation can be performed in a single step by mixing the resin with the catalyst in aqueous medium, followed by washing with water—or alternatively in two steps by first converting the resin to its hydroxyl form with a hydroxide such as aqueous sodium hydroxide, and then adding the catalyst.

The alkylene oxides used as starting material in the process of the invention have their conventional definition, i.e. they are compounds having a vicinal oxide (epoxy) group in their molecules.

Particularly suitable are alkylene oxides of the general formula

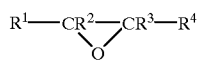

wherein $R^1$ to $R^4$ independently represent a hydrogen atom or an, optionally substituted, alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$–$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane, 2,3-epoxybutane and glycidol. Ethylene oxide and propylene oxide are of particular commercial importance.

As mentioned above, it is advantageous to perform the hydrolysis of the alkylene oxides, without using excessive amounts of water. In the process according to the present invention, amounts of water in the range of 1 to 15 moles per mole of alkylene oxide are quite suitable, amounts in the range of 1 to 6 on the same basis being preferred. In the process of the invention high selectivities with respect to the monoalkylene glycol are often already achieved, when only 4 or 5 moles of water per mole of alkylene oxide are supplied.

The process of the invention may be carried out in batch operation. However, in particular for large scale embodiments it is preferred to operate the process continuously.

Such continuous process can be carried out in a fixed bed reactor, operated in up-flow or down-flow. Down-flow operation is preferred.

The reactor may be maintained under isothermal, adiabatic or hybrid conditions. Isothermal reactors are generally shell- and tube reactors, mostly of the multitubular type, wherein the tubes contain the catalyst and a coolant passes outside the tubes. Adiabatic reactors are not cooled, and the product stream leaving them may be cooled in a separate heat exchanger.

Under certain chosen circumstances the catalytic conversion of ethylene oxide (EO) may be incomplete, in which situation rest EO can be thermally hydrolysed in the dead space of the reactor below the catalyst bed. Since this thermal hydrolysis is less specific towards monoethylene glycol (MEG), it is recommended to minimise the liquid hold-up in the reactor. This can be achieved by filing the reactor outlet part with internals or inert packing material to reduce its volume, and/or by adding an inert gas, such as nitrogen, to the reactor feed mixture and operating the reactor under so-called trickle flow conditions.

In order to obtain adequate time-yield values, it is recommended to perform the process under elevated temperature and pressure conditions.

Suitable reaction temperatures are generally in the range from 80 to 200° C., whereby temperatures in the range from 90 to 150° C. are preferred. The reaction pressure is usually selected in the range of 200 to 3000, preferably 200 to 2000 kPa. For batch operations of the process, the selected reaction pressure is advantageously obtained by pressurising with an inert gas, such as nitrogen. If desired, mixtures of gases may be used, for example a mixture of carbon dioxide and nitrogen is in certain instances advantageous.

In order to accommodate any swelling of the catalyst during operation, the reactor volume can advantageously be greater than the volume occupied by of the catalyst therein, for example 10 to 70 vol % greater.

It will be understood that the process of the present invention is not limited to its operation in the presence of the defined catalyst alone. In certain situations, particularly when operating in continuous-flow manner, it has been found to be advantageous to subject at least part, such as about 30–60 wt %, of the alkylene oxide feed stream to partial thermal hydrolysis in the absence of catalyst, before completing the hydrolysis catalytically. It has been found that partial hydrolysis, even in the absence of a catalyst, is still sufficiently selective towards the monoalkylene glycol while on the other hand this measure is effective in saving the catalyst.

A problem which may occasionally arise in any process wherein ethylene oxide is being hydrolysed is the presence of small amounts of amines and/or phosphines as impurities in the product stream. When a strongly basic anion exchange resin according to the present invention is used as the solid support for the catalytic anion, the basic groups thereof are quaternary phosphonium groups. It has been found that during operation, small amounts of phosphines may leach from the resin into the product stream. Besides, the product stream may contain small amounts of amines which originate from corrosion inhibitors added to the water used in the process. Although the amounts of such amine and/or phosphine contaminants reaching the end-product are generally very small, they may affect the quality of the end-product such that it may be desirable to keep them below the detection level. For example, trimethylamine (TMA) and/or dimethylamine (DMA) may reach the end-product in an amount of up to 10 ppm while the fishy odour of TMA may be detected in an amount as low as 1 ppb.

An effective measure in removing amines and/or phosphines which may be present in the product stream of generally any process wherein ethylene oxide is being hydrolysed, including the process of the present invention, has been found to be the use of a guard-bed, containing a strongly acidic ion exchange resin which effectively captures the amines or phosphines. Strongly acidic ion exchange resins are of the sulphonic type. Commercially available examples are those known by the trademarks AMBERLYST 15, AMBERJET 1500H, AMBERJET 1200H, DOWEX MSC-1, DOWEX 50W, DIANON SK1B, LEWATIT VP OC 1812, LEWATIT S 100 MB and LEWATIT S 100 G1. These strongly acidic ion exchange resins are available in $H^+$ form and in salt form, such as the $Na^+$ form. When only the $H^+$ form of the strongly acidic resin is used in the guard bed, the product stream after passing it may become acidic. Using a mixture of the strongly acidic ion exchange resin in its $H^+$ form and salt form has the advantage of the pH of the product stream remaining close to neutral.

An added advantage of the strongly acidic guard bed is that any remaining alkylene oxide which may be still present in the product stream is hydrolysed to alkylene glycol, albeit with a lesser selectivity towards the monoalkylene glycol.

In order to accommodate for exhaustion of the strongly acidic ion exchange resin during operation, it is advantageous to operate the guard bed in two or more separate vessels.

Exhausted strongly acidic ion exchange resin can be regenerated by treatment with an acid which is stronger than the sulphonic acid groups in the resin matrix, such as HCl and $H_2SO_4$. Hot sulphuric acid of 0.1–2 normality has been proven to be effective.

The following Examples will illustrate the invention.

EXAMPLES

1. Preparation of catalysts
1.1 Homogeneous bicarbonate catalysts

A quaternary phosphonium salt and a similar quaternary ammonium salt (for comparison) in hydroxide form were used as precursors for the bicarbonate catalysts under investigation:

tetra-n-butylphosphonium hydroxide: $(n-C_4H_9)_4P^+OH^-$
tetra-n-butylammonium hydroxide: $(n-C_4H_9)_4N^+OH^-$ These bases were converted into the bicarbonate salts prior to use by stirring overnight under 1000 kPa of carbon dioxide:

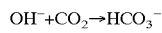
$$OH^- + CO_2 \rightarrow HCO_3^-$$

1.2 Catalysts based on strongly basic IER

A strongly basic ion exchange resin of the quaternary phosphonium type (tributylmethylphosphonium bromide on a polystyrene/1% divinylbenzene polymer support ex-Fluka, chloride form, exchange capacity 0.9 meq/g) was treated as follows to prepare the bicarbonate catalyst:

25 g of dry resin was stirred for 20 hours with 250 ml of demineralised water and 18.9 g (10 molar excess) of sodium bicarbonate ($NaHCO_3$). After filtration this procedure was repeated three times the exchanged resin was washed with 1200 ml of water for 2 hours until no more chloride could be detected (with the help of $AgNO_3$) in the wash water.

A strongly basic ion exchange resin of the quaternary phosphonium type (EGL-660, monodisperse cross-linked polystyrene/divinylbenzene resin ex-Rohm & Haas, chloride form, exchange capacity 1.7 meq/g) was treated as follows to prepare the formate catalyst:

100 g of wet (50 wt %) resin was slurried in a water filled glass tube (60×2.5 cm).

chloride was exchanged by treatment with 122.4 g sodium formate in aqueous solution (10 molar excess, in 2500 g of water) for approximately 5 hours (LHSV: 4 l/h).

the exchanged resin was washed with 1200 ml of water for 2 hours (LHSV: 4 l/h) until no more chloride could be detected (with the help of $AgNO_3$) in the wash water.

A strongly basic ion exchange resin of the quaternary ammonium type (AMBERJET 4200 (trademark), monodisperse cross-linked polystyrene/divinylbenzene resin ex-Rohm & Haas, chloride form, exchange capacity 1.4 meq/ml) was treated as follows to prepare the bicarbonate or formate catalyst for comparison:

150 ml of wet resin was slurried in a water filled glass tube (60×2.5 cm)

chloride was exchanged by treatment with 176.4 g of sodium bicarbonate or 151.2 g of sodium formate in aqueous solution (10 molar excess, in 2500 g of water) for approximately 5 hours (LHSV: 4 l/h)

the exchanged resin was washed with 1200 ml of water for 2 hours (LHSV: 4 l/h) until no more chloride could be detected (with the help of $AgNO_3$) in the wash water.

2. Batch EO hydrolysis reaction at 100° C.

A 250 ml autoclave was filled with the respective catalyst (30 mmol) and water (100 g; 5.55 mol). The gascap was purged 3 times with nitrogen and an initial pressure of 1000 kPa of $N_2$ was employed. In Exp. 2.3 and 2.4 the mixture was stirred overnight at room temperature under $CO_2$. In all cases the mixture was heated to 100° C. EO (44 g; 1 mol) was slowly added under stirring (500 rpm). The reaction mixture was maintained under continuous stirring for 6 hours at the reaction temperature. After cooling to room temperature (20° C.) stirring was continued overnight and an end of run sample was taken for GLC analysis.

The results of the catalytic EO batch hydrolysis experiments in terms of EO conversion and selectivity to MEG, using the phosphonium type of catalysts in bicarbonate form, and the results of reference experiments (no catalyst, $NaHCO_3$, AMBERJET 4200/bicarbonate and two tetraalkylammonium bicarbonate catalysts) are summarised in Table 1.

TABLE 1

Batch EO hydrolysis at 100° C. using phosphonium catalysts and comparison with similar ammonium catalysts.

| Exp. No. | Catalyst | Amount of catalyst (mmol) | EO conversion (mol %)* | Selectivity towards MEG (mol %)** |
|---|---|---|---|---|
| 2.1 (ref.) | — | — | 99.2 | 67.8 |
| 2.2 (ref.) | NaHCO$_3$ | 30 | 99.7 | 85.0 |
| 2.3 (ref.) | Tetra-n-butyl ammonium bicarbonate: (n-C$_4$H$_9$)$_4$N$^+$HCO$_3^-$ | 30.1 | >96 | 86.9 |
| 2.4 | Tetra-n-butyl phosphonium bicarbonate: (n-C$_4$H$_{93}$)$_4$P$^+$HCO$_3^-$ | 30 | >90 | 83.8 |
| 2.5 | Tributylmethyl phosphonium bicarbonate on PS/DVB (IER) | 19 | 99.9 | 87.1 |
| 2.6 (ref.) | AMBERJET 4200/HCO$_3^-$ (bicarbonate) | 30 | 99.0 | 88.3 |
| 2.7 | EGL-660/HCO$_2^-$ (formate) | 15 | 99.7 | 75.6 |
| 2.8 (ref.) | AMBERJET 4200/HCO$_2^-$ (formate) | 30 | 99.1 | 78.5 |

*EO conversion (mol %) = 100 × (MEG + 2DEG + 3TEG)/(EO + MEG + 2DEG + 3TEG)
**Selectivity towards MEG (mol %) = 100 × MEG/(MEG + 2DEG + 3TEG)

The results indicate that the phosphonium/bicarbonate catalysts (both homogeneous and on the polystyrene/divinylbenzene matrix) have a very attractive catalytic performance in terms of selectivity to MEG (83.8 and 87.1%, respectively). The performance is very similar to that of other bicarbonate type of catalysts.

3. Catalyst stability test

In order to compare the thermal stability of a quaternary phosphonium compounds with a similar quaternary ammonium compound, both were studied in hydroxide form, because such hydroxides are more sensitive to thermal degradation than the respective bicarbonate forms.

The thermal stability of tetrabutyl phosphonium hydroxide (TBPH) was evaluated and compared with the thermal stability of tetrabutyl ammonium hydroxide (TBAH). The hydroxides (a 40% aqueous solution of each) were kept at 100° C. in an autoclave for several days. At time intervals samples were taken for analysis. The decomposition of the quaternary bases was determined by Nuclear Magnetic Resonance (NMR) spectroscopy, using Carbon-13 ($^{13}$C) NMR for the ammonium compounds and Phosphorus-31 ($^{31}$P) NMR for the phosphonium compounds.

The NMR analysis showed that the thermal degradation product of the quaternary ammonium hydroxide TBAH was tri-n-butylamine (TBA), and that the thermal degradation product of the quaternary phosphonium hydroxide TBPH was tri-n-butylphosphine oxide (TBPO).

The results of these stability studies are summarised in Table 2.

TABLE 2

Thermal stability test of a quaternary phosphonium catalyst in comparison with a similar quaternary ammonium catalyst

| Time (h) | TBPH (% mol) | TBPO (% mol) | TBAH (% mol) | TBA (% mol) |
|---|---|---|---|---|
| 0 | 100 | 0 | 100 | 0 |
| 3–4 | 95 | 1 | 94 | 0 |
| 20–21 | 93 | 3 | 94 | 0.3 |
| 44–46 | 90 | 6 | 96 | 0.8 |
| 116–120 | 78 | 18 | 41 | 58 |

These results indicate that the thermal stability of a quaternary phosphonium compound is significantly better than the thermal stability of a similar quaternary ammonium compound.

What is claimed is:

1. A process for the preparation of alkylene glycols by reacting an alkylene oxide with water in the presence of at least one ionic composition of a quaternary phosphonium cation of the general formula $$R_1R_2R_3R_4P^+$$

whereby each of $R_1$, $R_2$, $R_3$ and $R_4$, independently, is an alkyl, cycloalkyl, aryl, alkylaryl or arylalkyl group having from 1 to 10 carbon atoms, each of which may carry one or more substituents or be attached to a polymer, and an anion other than metalate or halogen.

2. A process according to claim 1, whereby the anion comprises bicarbonate, bisulphite or carboxylic acid derivatives.

3. A process according to claim 2, whereby the anion comprises a formate or citrate anion.

4. A process according to claim 1, whereby the quaternary phosphonium cation is immobilised on a solid support.

5. A process according to claim 4, whereby the solid support is an anion exchange resin.

* * * * *